United States Patent
Hirson et al.

(10) Patent No.: US 9,561,486 B2
(45) Date of Patent: Feb. 7, 2017

(54) SYSTEM FOR GENERATING FUEL MATERIALS USING FISCHER-TROPSCH CATALYSTS AND PLASMA SOURCES

(71) Applicant: POWERDYNE, INC., Newport Beach, CA (US)

(72) Inventors: Geoffrey Hirson, Newport Beach, CA (US); Gus F. Shouse, Newport Beach, CA (US)

(73) Assignee: Powerdyne, Inc., Newport Beach, CA (US)

( * ) Notice: Subject to any disclaimer, the term of this patent is extended or adjusted under 35 U.S.C. 154(b) by 0 days.

(21) Appl. No.: 14/426,268

(22) PCT Filed: Sep. 5, 2013

(86) PCT No.: PCT/US2013/058335
§ 371 (c)(1),
(2) Date: Mar. 5, 2015

(87) PCT Pub. No.: WO2014/039726
PCT Pub. Date: Mar. 13, 2014

(65) Prior Publication Data
US 2015/0231593 A1    Aug. 20, 2015

Related U.S. Application Data

(60) Provisional application No. 61/697,148, filed on Sep. 5, 2012.

(51) Int. Cl.
B01J 19/08    (2006.01)
C10G 2/00    (2006.01)
B01J 12/00    (2006.01)

(52) U.S. Cl.
CPC ........... *B01J 19/088* (2013.01); *B01J 12/00* (2013.01); *C10G 2/341* (2013.01);
(Continued)

(58) Field of Classification Search
CPC ............. B01J 19/088; B01J 2219/0898; B01J 2219/0805; B01J 2219/0869; B01J 2219/00058; B01J 2219/00164; B01J 2219/00162
See application file for complete search history.

(56) References Cited

U.S. PATENT DOCUMENTS 1,746,464 A    2/1930  Fischer et al.
3,979,205 A    9/1976  Wanzenberg
(Continued)

FOREIGN PATENT DOCUMENTS

CA    2379892 A1    2/2001
CN    1268550 A    10/2000
(Continued)

OTHER PUBLICATIONS

International Search Report and Written Opinion dated Jul. 28, 2014 for International Application No. PCT/US2014/024606.
(Continued)

*Primary Examiner* — Kishor Mayekar
(74) *Attorney, Agent, or Firm* — Pepper Hamilton LLP

(57) ABSTRACT

In a first processing chamber, a feedstock may be combined with plasma from, for example, three plasma torches to form a first fluid mixture. Each torch may have a working gas including water vapor, oxygen, and carbon dioxide. The first fluid mixture may be cooled and may contact a first heat exchange device. The output fluid from the first heat exchange device may be separated into one or more components. A syngas may be derived from the one or more components and have a ratio of carbon monoxide to hydrogen of about 1:2. The syngas may be transferred to a catalyst bed to be converted into one or more fluid fuels.

24 Claims, 2 Drawing Sheets

(52) U.S. Cl.
CPC .......... *B01J 2219/00058* (2013.01); *B01J 2219/00162* (2013.01); *B01J 2219/00164* (2013.01); *B01J 2219/0805* (2013.01); *B01J 2219/0869* (2013.01); *B01J 2219/0898* (2013.01)

(56) References Cited

U.S. PATENT DOCUMENTS

| | | | |
|---|---|---|---|
| 4,466,807 A | 8/1984 | Santen et al. | |
| 4,508,040 A | 4/1985 | Santen et al. | |
| 4,591,428 A | 5/1986 | Pronk | |
| 4,770,109 A | 9/1988 | Schlienger | |
| 4,831,944 A | 5/1989 | Durand et al. | |
| 4,845,334 A | 7/1989 | Stocks et al. | |
| 4,898,748 A | 2/1990 | Kruger, Jr. | |
| 5,046,144 A | 9/1991 | Jensen | |
| 5,107,517 A | 4/1992 | Lauren | |
| 5,136,137 A | 8/1992 | Schlienger | |
| 5,138,959 A | 8/1992 | Kulkarni | |
| 5,288,969 A | 2/1994 | Wong et al. | |
| 5,301,620 A | 4/1994 | Nagel et al. | |
| 5,319,176 A | 6/1994 | Alvi et al. | |
| 5,493,578 A | 2/1996 | Fukusaki et al. | |
| 5,534,659 A | 7/1996 | Springer et al. | |
| 5,541,386 A | 7/1996 | Alvi et al. | |
| 5,544,597 A | 8/1996 | Camacho | |
| 5,611,947 A | 3/1997 | Vavruska | |
| 5,634,414 A | 6/1997 | Camacho | |
| 5,666,891 A * | 9/1997 | Titus | A62D 3/19 110/250 |
| 5,673,635 A | 10/1997 | Fowler | |
| 5,725,616 A | 3/1998 | Lynum et al. | |
| 5,798,496 A | 8/1998 | Eckhoff et al. | |
| 5,898,027 A | 4/1999 | Bardenberg et al. | |
| 5,935,293 A | 8/1999 | Detering et al. | |
| 5,958,264 A | 9/1999 | Tsantrizos et al. | |
| 6,127,645 A | 10/2000 | Titus et al. | |
| 6,153,852 A | 11/2000 | Blutke et al. | |
| 6,173,002 B1 | 1/2001 | Robert | |
| 6,187,226 B1 | 2/2001 | Detering et al. | |
| 6,215,678 B1 | 4/2001 | Titus et al. | |
| 6,289,851 B1 | 9/2001 | Rabovitser et al. | |
| 6,355,904 B1 | 3/2002 | Batdorf et al. | |
| 6,372,156 B1 | 4/2002 | Kong et al. | |
| 6,375,832 B1 | 4/2002 | Eliasson et al. | |
| 6,505,567 B1 | 1/2003 | Anderson et al. | |
| 6,524,538 B2 | 2/2003 | Barankova et al. | |
| 6,552,295 B2 | 4/2003 | Markunas et al. | |
| 6,810,821 B2 | 11/2004 | Chan | |
| 6,821,500 B2 | 11/2004 | Fincke et al. | |
| 6,874,434 B1 | 4/2005 | Bigelow et al. | |
| 6,971,323 B2 | 12/2005 | Capote et al. | |
| 6,976,362 B2 | 12/2005 | Sheppard et al. | |
| 6,987,792 B2 | 1/2006 | Do et al. | |
| 7,070,634 B1 | 7/2006 | Wang | |
| 7,097,675 B2 | 8/2006 | Detering et al. | |
| 7,279,655 B2 | 10/2007 | Blutke et al. | |
| 7,335,320 B2 | 2/2008 | Kindig et al. | |
| 7,384,619 B2 | 6/2008 | Bar-Gadda | |
| 7,576,296 B2 | 8/2009 | Fincke et al. | |
| 7,622,693 B2 | 11/2009 | Foret | |
| 7,674,443 B1 | 3/2010 | Davis | |
| 7,832,344 B2 | 11/2010 | Capote et al. | |
| 7,845,411 B2 | 12/2010 | Vinegar et al. | |
| 7,981,371 B2 | 7/2011 | Meillot et al. | |
| 8,129,654 B2 | 3/2012 | Lee et al. | |
| 8,168,128 B2 | 5/2012 | Seely et al. | |
| 8,199,790 B2 | 6/2012 | Vera | |
| 8,216,433 B2 | 7/2012 | Yonesu | |
| 8,252,244 B2 | 8/2012 | Capote et al. | |
| 8,268,094 B2 | 9/2012 | Zurecki et al. | |
| 8,277,631 B2 | 10/2012 | Eastman et al. | |
| 8,303,916 B2 | 11/2012 | Collins et al. | |
| 8,324,523 B2 | 12/2012 | Foret | |
| 8,357,873 B2 | 1/2013 | Foret | |
| 8,367,005 B2 | 2/2013 | Ikeda et al. | |
| 8,475,551 B2 | 7/2013 | Tsangaris et al. | |
| 8,518,162 B2 | 8/2013 | Smith et al. | |
| 8,519,354 B2 | 8/2013 | Charipar et al. | |
| 2002/0000085 A1 | 1/2002 | Hall et al. | |
| 2002/0040889 A1 | 4/2002 | Markunas et al. | |
| 2002/0151604 A1 | 10/2002 | Detering et al. | |
| 2003/0029796 A1 | 2/2003 | Maekawa | |
| 2003/0065042 A1 | 4/2003 | Shaw | |
| 2003/0209174 A1 | 11/2003 | Chan | |
| 2004/0134517 A1 | 7/2004 | Clark | |
| 2004/0251241 A1 | 12/2004 | Blutke et al. | |
| 2006/0053791 A1 | 3/2006 | Prentice, III | |
| 2006/0060464 A1 | 3/2006 | Chang | |
| 2006/0112639 A1 | 6/2006 | Nick et al. | |
| 2006/0201157 A1 | 9/2006 | Villalobos | |
| 2006/0233699 A1 | 10/2006 | Mills | |
| 2007/0017228 A1 | 1/2007 | Surma | |
| 2007/0186474 A1 | 8/2007 | Rabovitser et al. | |
| 2007/0253874 A1 | 11/2007 | Foret | |
| 2007/0258869 A1 | 11/2007 | Tsangaris et al. | |
| 2007/0266633 A1 | 11/2007 | Tsangaris et al. | |
| 2007/0267289 A1 | 11/2007 | Jabs et al. | |
| 2007/0272131 A1 | 11/2007 | Carabin et al. | |
| 2008/0041829 A1 | 2/2008 | Blutke et al. | |
| 2008/0083701 A1 | 4/2008 | Shao et al. | |
| 2008/0147241 A1 | 6/2008 | Tsangaris et al. | |
| 2008/0184621 A1 | 8/2008 | Clark | |
| 2008/0202028 A1 | 8/2008 | Tsangaris et al. | |
| 2008/0209807 A1 | 9/2008 | Tsangaris et al. | |
| 2008/0222956 A1 | 9/2008 | Tsangaris et al. | |
| 2008/0223047 A1 | 9/2008 | Oliver | |
| 2008/0277265 A1 | 11/2008 | Tsangaris et al. | |
| 2008/0283153 A1 | 11/2008 | Zurecki et al. | |
| 2008/0283411 A1 | 11/2008 | Eastman et al. | |
| 2008/0290322 A1 | 11/2008 | Hederer et al. | |
| 2009/0038958 A1 | 2/2009 | Coyle et al. | |
| 2009/0133407 A1 | 5/2009 | Sawyer | |
| 2009/0183430 A1* | 7/2009 | Schubert | C10J 3/04 48/85 |
| 2009/0188127 A1 | 7/2009 | Gorbell et al. | |
| 2009/0307975 A1 | 12/2009 | Wolf | |
| 2010/0050654 A1 | 3/2010 | Chiu et al. | |
| 2010/0065781 A1 | 3/2010 | Brothier | |
| 2010/0167139 A1 | 7/2010 | Gattis et al. | |
| 2010/0229522 A1 | 9/2010 | Kingzett | |
| 2010/0298449 A1 | 11/2010 | Rojey | |
| 2011/0067376 A1 | 3/2011 | Tompkins et al. | |
| 2011/0162523 A1* | 7/2011 | Fabbri | B01D 53/32 95/73 |
| 2011/0162958 A1 | 7/2011 | Cho et al. | |
| 2011/0201700 A1* | 8/2011 | Lucas | C07C 29/1518 518/702 |
| 2011/0212012 A1 | 9/2011 | McAlister | |
| 2011/0265698 A1 | 11/2011 | Hirson et al. | |
| 2011/0286893 A1 | 11/2011 | Zimmerman et al. | |
| 2012/0000115 A1 | 1/2012 | Shastri | |
| 2012/0032452 A1 | 2/2012 | Kuku | |
| 2012/0070347 A1 | 3/2012 | Bacon et al. | |
| 2012/0090985 A1 | 4/2012 | Rabinovich et al. | |
| 2012/0114877 A1 | 5/2012 | Lee | |
| 2012/0121468 A1 | 5/2012 | Tsangaris et al. | |
| 2012/0291436 A1 | 11/2012 | Hirson et al. | |
| 2013/0200624 A1 | 8/2013 | Hirson et al. | |
| 2013/0300121 A1 | 11/2013 | Ali et al. | |

FOREIGN PATENT DOCUMENTS

| | | |
|---|---|---|
| CN | 1810938 A | 8/2006 |
| EP | 1270508 A1 | 1/2003 |
| GB | 573982 | 12/1945 |
| WO | WO 2005/005009 A2 | 1/2005 |
| WO | WO 2008/130260 A1 | 10/2008 |
| WO | WO 2009/156761 A2 | 12/2009 |
| WO | WO 2010/056462 A1 | 5/2010 |
| WO | WO 2011/091327 A1 | 7/2011 |
| WO | WO 2011/140080 A2 | 11/2011 |
| WO | WO 2012/039751 A2 | 3/2012 |
| WO | WO 2012/064936 A1 | 5/2012 |

(56) References Cited

FOREIGN PATENT DOCUMENTS

| WO | WO 2012/077198 A1 | 6/2012 |
|---|---|---|
| WO | WO 2012/158797 A1 | 11/2012 |
| WO | WO 2012/177666 A1 | 12/2012 |

OTHER PUBLICATIONS

International Search Report and Written Opinion dated Jan. 16, 2014 for International Application No. PCT/US2013/058335.
Plasco Group, "How is Plasco Different?," http://www.plascoenergygroup.com/our-solution/how-is-plasco-different/, retrieved from web Jul. 5, 2011.
Schuey et al., "LLW Processing and Operational Experience Using a Plasma ARC Centrifugal Treatment (PACT) System," *WM'06 Conference*, Feb. 26-Mar. 2, 2006, Tucson, AZ.
Urashima et al., "Removal of Volatile Organic Compounds from Air Streams and Industrial Flue Gases by Non-Thermal Plasma Technology," *IEEE Transactions on Dielectrics and Electrical Insulation*, Oct. 2000, 7(5):602-614.
International Search Report and Written Opinion dated Feb. 24, 2015 for International Application No. PCT/US2014/069342.
"C-17 flight uses synthetic fuel blend," (Oct. 25, 2007), Wright-Patterson Air Force Base, Retrieved Feb. 7, 2008, http://www.wpafb.af.mil/news/story.asp?id=123073170.
Fairley, Peter, "Growing Biofuels," (Nov. 23, 2005), MIT Technology Review, http://www.technologyreview.com/news/404941/growing-biofuels/.
"Governor Rendell leads with innovative solution to help address PA energy needs," State of Pennsylvania. Archived from original on Dec. 11, 2008, http://web.archive.org/web/20081211180710/http://www.state.pa.us/papower/cwp/view.asp?Q=446127&A=11.
Jamieson et al., "Keeping the Options Open", *Petroleum Economist*, Retrieved LNG 2012.
Krauss, Clifford, "South African Company to Build U.S. Plant to Convert Gas to Liquid Fuels," (Dec. 3, 2012), *New York Times*, http://www.mytimes.com/2012/12/04/business/energy-environment/sasol-plans-first-gas-to-liquids-plant-in-us.html?_r=1.
Lane, Jim, "Little Big Tech: Can Fischer-Tropsch technology work at smaller scale?" (Nov. 20, 2012), *Biofuels Digest*, http://www.biofuelsdigest.com/bdigest/2012/11/20/little-big-tech-can-fischer-tropsch-technology-work-at-smaller-scale/.
"PetroSA Wins Innovation Award," SouthAfrica.info, (Oct. 10, 2008), Retrieved Dec. 18, 2012, http://www.southafrica.info/business/trends/innovations/petrosa-101008.htm.
"PetroSA technology ready for next stage," Businessday.co.za, (May 10, 2011) Retrieved Jun. 5, 2013, http://www.bdlive.co.za/articles/2011/05/10/petrosa-technology-ready-for-next-stage.
Pitt, Anthea, "Linc gears up for Chinchilla GTL," (Nov. 28, 2012), Upstreamonline.com, http://www.upstreamonline.com/live/article1149671.ece?print=preview.
"Schweitzer wants to convert Otter Creek coal into liquid fuel," (Aug. 2, 2005), *Billings Gazette*, Archived from original on Jan. 1, 2009.
Smedley, Mark, "Small GTL's Market Reach as Great as Opec's, UK Firm Says," *World Gas Intelligence*, Retrieved Dec. 19, 2012, http://www.oxfordcatalysts.com/press/egs/world_gas_intelligence_121219.pdf.
Steynberg et al., "Clean Coal Conversion Options Using Fischer-Tropsch Technology," (2003), Fuel Chemistry Division Preprints, 48(1); 459-461.
"UPM-Kymmene says to establish beachhead in biodesel market," NewsRoom Finland. Archived from original on Mar. 17, 2007, http://web.archive.org/web/20070317104947/http:/newsroom.finland.fi/stt/showarticle.asp?intNWSAID=14179&group=Business.
Supplemental European Search Report for EP13836174 dated Mar. 31, 2016.
Supplemental European Search Report for EP 13835933 dated Mar. 31, 2016.
Supplemental European Search Report for EP 13834468 dated Mar. 31, 2016.
Supplemental European Search Report for EP 13834969 dated Apr. 1, 2016.
Supplemental European Search Report for EP 13835425 dated Apr. 1, 2016.
Supplemental European Search Report for EP 13835534 dated Apr. 11, 2016.
Supplemental European Search Report for EP 13835723 dated Mar. 31, 2016.

\* cited by examiner

US 9,561,486 B2

SYSTEM FOR GENERATING FUEL MATERIALS USING FISCHER-TROPSCH CATALYSTS AND PLASMA SOURCES

CLAIM OF PRIORITY

This application is a national phase application under 35 U.S.C. §371 of International Application No. PCT/US2013/058335, entitled "System for Generating Fuel Materials Using Fischer-Tropsch Catalysts and Plasma Sources," and filed Sep. 5, 2013, which claims the benefit of and priority to U.S. Provisional Patent Application No. 61/697,148, entitled "Methods for Generating Fuel Materials and Power, and Sequestering Toxins Using Plasma Sources," which was filed on Sep. 5, 2012. The aforementioned applications are incorporated by reference herein in their entireties and for all purposes.

BACKGROUND

Fuel materials may take on a variety of forms, from simple gases such as hydrogen to complex mixtures including aviation fuels. Due to their wide range of chemical compositions, chemical fuels may be generated through a variety of processes and may require facilities dedicated to synthesizing only a small number of possible fuel types. Such facilities may be optimized to generate only the fuels to which they are dedicated. Additionally, each facility may require a specific set of feed-stocks or precursor materials for fuel synthesis.

Typically, carbon-based fuels rely on thermal methods for their synthesis. Such methods may include pyrolysis, cracking, and endothermic synthesis steps. Such processes may generate excessive heat as a by-product of their synthetic methods. Further, such thermal chemistry-based synthetic methods may not be efficient even for an optimized facility.

It is therefore desirable to develop high efficiency methods for generating a variety of gaseous and/or liquid fuels from a limited number of readily available feed stocks.

SUMMARY

In an embodiment, a system for synthesizing a fuel fluid may include a first processing chamber, one or more controllable plasma sources, in which each of the controllable plasma sources is configured to deliver a plasma discharge into the first processing chamber, one or more controllable sources of working fluids, in which each of the controllable sources of working fluids is configured to deliver an amount of a working fluid to a corresponding controllable plasma source, a first heat exchange device in fluid communication with the first processing chamber, a coolant addition device in fluid communication with the first processing chamber and the first heat exchange device, a gas separator configured to receive a second fluid mixture from an output port of the first heat exchange device and to separate the second fluid mixture into one or more components, one or more gas holding containers to store the one or more components of the second fluid mixture, a catalyst bed configured to receive a portion of the one or more components of the second fluid mixture and to convert the portion of the one or more components into a fuel fluid, a number of sensors configured to sense at least one process control variable associated with one or more of the first processing chamber, the one or more controllable plasma sources, the one or more controllable sources of working fluids, the coolant addition device, and the first heat exchange device, at least one electronic device configured to receive information from the sensors and to control one or more of the one or more controllable plasma sources, one or more controllable sources of working fluids, and the first heat exchange device, and at least one receptacle configured to receive the fuel fluid.

DETAILED DESCRIPTION

Figure 1A:
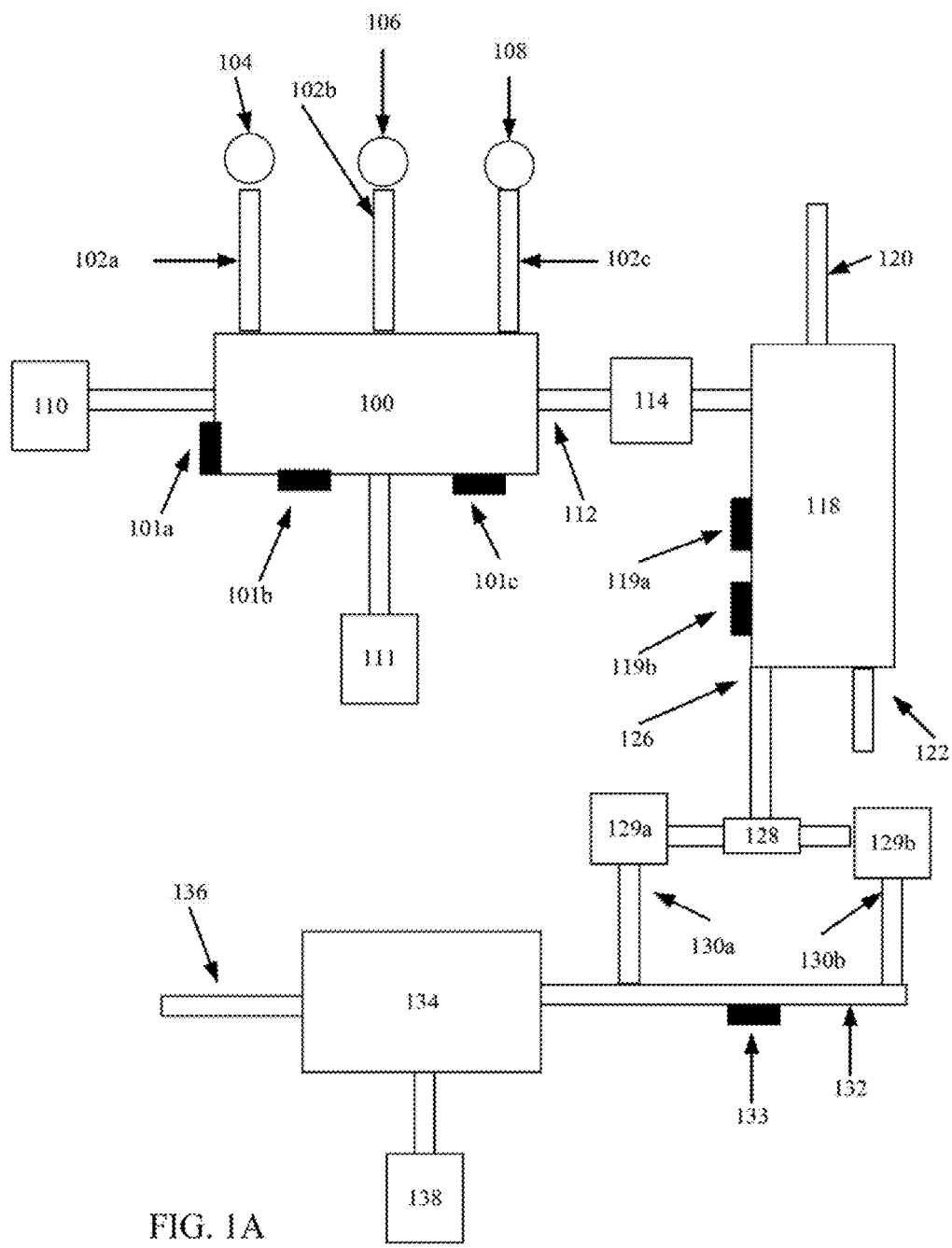
FIG. 1A illustrates an embodiment of a system for fabricating one or more fuel materials from at least one plasma source and a carbon feedstock in accordance with the present disclosure.

FIG. 1A illustrates an embodiment of a system fabricating one or more fuel materials from $H_2O$, $CO_2$, $O_2$, and a carbon feedstock. Improved efficiency may be obtained in part by having the fuel generating facility also produce at least some electric power to lessen the facility's dependence on exterior power supplies. Improved efficiency may also be obtained by a facility having multiple points of process control to properly adjust reaction temperatures and other process conditions to optimize the processes.

Within a first processing chamber 100, a first fluid plasma, a second fluid plasma, and a third fluid plasma may be introduced. The first fluid plasma may be generated by exposing a first working fluid to a first high voltage electric field, such as may be generated by a first plasma torch 102a, the second fluid plasma may be generated by exposing a second working fluid to a second high voltage electric field, such as may be generated by a second plasma torch 102b, and the third fluid plasma may be generated by exposing a third working fluid to a third high voltage electric field, such as may be generated by a third plasma torch 102c. In some embodiments, the first working fluid may be carbon dioxide gas ($CO_2$), the second working fluid may be oxygen gas ($O_2$), and the third working fluid may be water vapor ($H_2O$). Alternative working fluids may also include one or more of ethanol, methanol, and natural gas. In some embodiments, the first fluid plasma, second fluid plasma, and third fluid plasma may each attain a temperature of about 20,000 degrees C. at the output of their respective plasma torches (102a, 102b, and 102c). In another embodiment, the first fluid plasma, second fluid plasma, and third fluid plasma may each attain a temperature of about 4000° C. to about 20000° C.

Figure 1B:
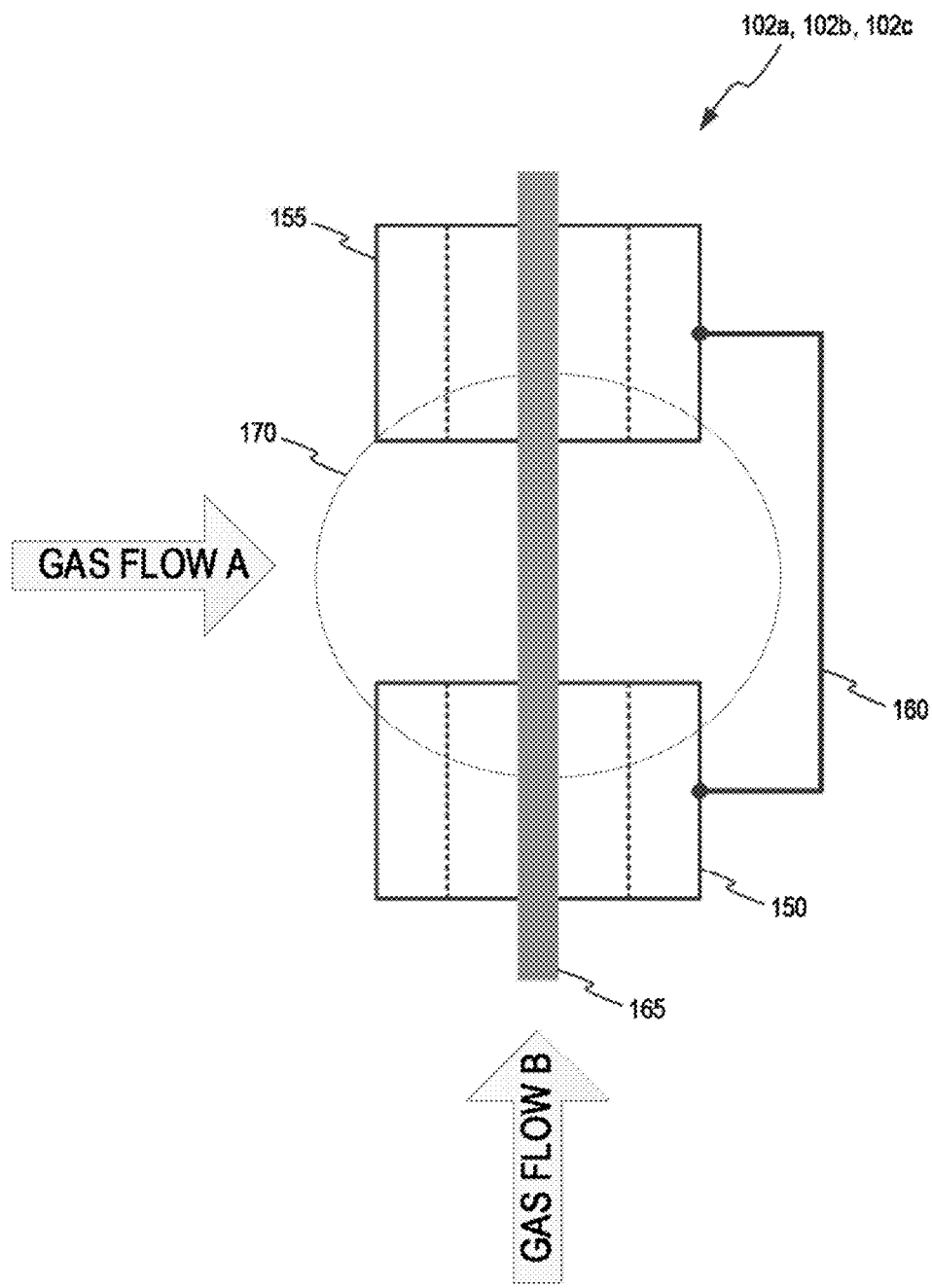
FIG. 1B depicts a block diagram of an illustrative high-voltage electric field generator according to an embodiment.

Each of the one or more high-voltage electric field generators 102a, 102b, 102c may generally be any of various components that may be used to generate a high voltage potential. Thus, as shown in FIG. 1B, each of the one or more high-voltage electric field generators 102a, 102b, 102c may have at least one anode surface 150, at least one cathode surface 155, and an electric potential 160 between the anode surface and the cathode surface. As a result, a magnetic field 165 and an electric field 170 may be generated when the electric potential 160 is applied between the at least one anode surface 150 and the at least one cathode surface 155. In some embodiments, a flow of gas, as described in greater detail herein and indicated by the horizontal arrow, may be substantially perpendicular to the magnetic field 165. In other embodiments, the flow of gas, as indicated by the vertical arrow, may be substantially parallel to the magnetic field 165. The magnetic field 165 and the electric field 170 may each have an effect on gas that flows through a gap between the anode surface 150 and the cathode surface 155. In a non-limiting example, the electric field 170 may stabilize the gas and/or ionize the gas. In another non-limiting example, the magnetic field 165 may alter a spin and/or a velocity of the gas.

It may be appreciated that the $CO_2$, $O_2$, and $H_2O$ in the first processing chamber 100 may be used as working fluids for their respective plasma torches (102a, 102b, and 102c). Thus, each gas may be exposed to high voltage electric fields. As a result of exposure to such fields, the gases may be reduced to free radical species (as examples, for $H_2O$, these may include the hydroxyl radical OH*, and for $O_2$ these may include the superoxide anion radical $O2^{*-}$) in addition to ionized species (for $O_2$, these may include $O^-$, $O_2^-$, $O_2^+$, and $O^+$). The types and amounts of reactive species created by exposure of the gases to high voltage electric fields may differ from those generated by exposure of the gases to heat alone.

In one non-limiting example of the method, exposing the first working fluid to a first high voltage electric field may include providing an anode surface and a cathode surface separated by a distance to create a gap between the two surfaces. A first high voltage electric potential may be induced between the anode surface and the cathode surface, and the first working fluid may be induced to traverse the gap between the two surfaces. The gap may generally be selected such that (for the electrical voltage selected), the electrical field is about 0.3 kV/cm to about 8.0 kV/cm, including about 0.3 kV/cm, about 0.3149 kV/com, about 0.5 kV/cm, about 0.75 kV/com, about 1.0 kV/com, about 1.25 kV/cm, about 1.5 kV/cm, about 1.574 kV/cm, about 2.0 kV/com, about 2.5 kV/cm, about 3.0 kV/cm, about 0.3149 kV/cm, about 3.5 kV/cm, about 4.0 kV/cm, about 4.5 kV/cm, about 5.0 kV/cm, about 5.5 kV/cm, about 6.0 kV/cm, about 6.5 kV/cm, about 7.0 kV/cm, about 7.5 kV/cm, about 7.559 kV/cm, about 8.0 kV/cm, or any value or range between any two of these values (including endpoints). Illustrative distances may be about 0.15 cm to about 0.65 cm, including about 0.15 cm, about 0.20 cm, about 0.25 cm, about 0.30 cm, about 0.3175 cm, about 0.35 cm, about 0.40 cm, about 0.45 cm, about 0.50 cm, about 0.55 cm, about 0.60 cm, about 0.65 cm, or any value or range between any two of these values (including endpoints). Thus, to achieve a desired electrical field, a voltage potential may be provided between the anode surface and the cathode surface. For example, a first high voltage electric potential may be induced between the anode surface and the cathode surface, and the first working fluid may be induced to traverse the gap between the two surfaces. In one non-limiting embodiment, the high voltage potential may be about 2.4 kV times the gap distance in centimeters to about 60 kV times the gap distance in centimeters, including about 2.4 kV, about 5 kV, about 10 kV, about 20 kV, about 30 kV, about 40 kV, about 50 kV, about 60kV, or any value or range between any two of these values (including endpoints). Thus, for example, a voltage between the anode surface and the cathode surface (which is 0.3175 cm) is 2.4 kV, thereby resulting in an electrical field of about 7.559 kV/cm. In another non-limiting embodiment, the high-voltage electric potential may be an alternating current (AC) potential having a frequency of about 1 MHz to about 50 MHz, including about 1 MHz, about 5 MHz, about 10 MHz, about 20 MHz, about 25 MHz, about 30 MHz, about 40 MHz, about 50 MHz, or any value or range between any two of these values (including endpoints). In another non-limiting embodiment, the high-voltage electric potential may have a current of about 100 Amperes to about 1000 Amperes, including about 100 Amperes, about 200 Amperes, about 300 Amperes, about 400 Amperes, about 500 Amperes, about 600 Amperes, about 700 Amperes, about 800 Amperes, about 900 Amperes, about 1000 Amperes, or any value or range between any two of these values (including endpoints).

In another non-limiting example of the method, exposing the second working fluid to a second high voltage electric field may include providing an anode surface and a cathode surface separated by a distance to create a gap between the two surfaces. A second high voltage electric potential may be induced between the anode surface and the cathode surface, and the second working fluid may be induced to traverse the gap between the two surfaces. The gap may generally be selected such that (for the electrical voltage selected), the electrical field is about 0.3 kV/cm to about 8.0 kV/cm, including about 0.3 kV/cm, about 0.3149 kV/com, about 0.5 kV/cm, about 0.75 kV/com, about 1.0 kV/com, about 1.25 kV/cm, about 1.5 kV/cm, about 1.574 kV/cm, about 2.0 kV/com, about 2.5 kV/cm, about 3.0 kV/cm, about 0.3149 kV/cm, about 3.5 kV/cm, about 4.0 kV/cm, about 4.5 kV/cm, about 5.0 kV/cm, about 5.5 kV/cm, about 6.0 kV/cm, about 6.5 kV/cm, about 7.0 kV/cm, about 7.5 kV/cm, about 7.559 kV/cm, about 8.0 kV/cm, or any value or range between any two of these values (including endpoints). Illustrative distances may be about 0.15 cm to about 0.65 cm, including about 0.15 cm, about 0.20 cm, about 0.25 cm, about 0.30 cm, about 0.3175 cm, about 0.35 cm, about 0.40 cm, about 0.45 cm, about 0.50 cm, about 0.55 cm, about 0.60 cm, about 0.65 cm, or any value or range between any two of these values (including endpoints). Thus, to achieve a desired electrical field, a voltage potential may be provided between the anode surface and the cathode surface. For example, a second high voltage electric potential may be induced between the anode surface and the cathode surface, and the second working fluid may be induced to traverse the gap between the two surfaces. In one non-limiting embodiment, the high voltage potential may be about 2.4 kV times the gap distance in centimeters to about 60 kV times the gap distance in centimeters, including about 2.4 kV, about 5 kV, about 10 kV, about 20 kV, about 30 kV, about 40 kV, about 50 kV, about 60kV, or any value or range between any two of these values (including endpoints). Thus, for example, a voltage between the anode surface and the cathode surface (which is 0.3175 cm) is 2.4 kV, thereby resulting in an electrical field of about 7.559 kV/cm. In another non-limiting embodiment, the high-voltage electric potential may be an alternating current (AC) potential having a frequency of about 1 MHz to about 50 MHz, including about 1 MHz, about 5 MHz, about 10 MHz, about 20 MHz, about 25 MHz, about 30 MHz, about 40 MHz, about 50 MHz, or any value or range between any two of these values (including endpoints). In another non-limiting embodiment, the high-voltage electric potential may have a current of about 100 Amperes to about 1000 Amperes, including about 100 Amperes, about 200 Amperes, about 300 Amperes, about 400 Amperes, about 500 Amperes, about 600 Amperes, about 700 Amperes, about 800 Amperes, about 900 Amperes, about 1000 Amperes, or any value or range between any two of these values (including endpoints).

In another non-limiting example of the method, exposing the third working fluid to a third high voltage electric field may include providing an anode surface and a cathode surface separated by a distance to create a gap between the two surfaces. A third high voltage electric potential may be induced between the anode surface and the cathode surface, and the third working fluid may be induced to traverse the gap between the two surfaces The gap may generally be selected such that (for the electrical voltage selected), the electrical field is about 0.3 kV/cm to about 8.0 kV/cm, including about 0.3 kV/cm, about 0.3149 kV/com, about 0.5 kV/cm, about 0.75 kV/com, about 1.0 kV/com, about 1.25 kV/cm, about 1.5 kV/cm, about 1.574 kV/cm, about 2.0 kV/com, about 2.5 kV/cm, about 3.0 kV/cm, about 0.3149 kV/cm, about 3.5 kV/cm, about 4.0 kV/cm, about 4.5 kV/cm, about 5.0 kV/cm, about 5.5 kV/cm, about 6.0 kV/cm, about 6.5 kV/cm, about 7.0 kV/cm, about 7.5 kV/cm, about 7.559 kV/cm, about 8.0 kV/cm, or any value or range between any two of these values (including endpoints). Illustrative distances may be about 0.15 cm to about 0.65 cm, including about 0.15 cm, about 0.20 cm, about 0.25 cm, about 0.30 cm, about 0.3175 cm, about 0.35 cm, about 0.40 cm, about 0.45 cm, about 0.50 cm, about 0.55 cm, about 0.60 cm, about 0.65 cm, or any value or range between any two of these values (including endpoints). Thus, to achieve a desired electrical field, a voltage potential may be provided between the anode surface and the cathode surface. For example, a third high voltage electric potential may be induced between the anode surface and the cathode surface, and the third working fluid may be induced to traverse the gap between the two surfaces. In one non-limiting embodiment, the high voltage potential may be about 2.4 kV times the gap distance in centimeters to about 60 kV times the gap distance in centimeters, including about 2.4 kV, about 5 kV, about 10 kV, about 20 kV, about 30 kV, about 40 kV, about 50 kV, about 60kV, or any value or range between any two of these values (including endpoints). Thus, for example, a voltage between the anode surface and the cathode surface (which is 0.3175 cm) is 2.4 kV, thereby resulting in an electrical field of about 7.559 kV/cm. In another non-limiting embodiment, the high-voltage electric potential may be an alternating current (AC) potential having a frequency of about 1 MHz to about 50 MHz, including about 1 MHz, about 5 MHz, about 10 MHz, about 20 MHz, about 25 MHz, about 30 MHz, about 40 MHz, about 50 MHz, or any value or range between any two of these values (including endpoints). In another non-limiting embodiment, the high-voltage electric potential may have a current of about 100 Amperes to about 1000 Amperes, including about 100 Amperes, about 200 Amperes, about 300 Amperes, about 400 Amperes, about 500 Amperes, about 600 Amperes, about 700 Amperes, about 800 Amperes, about 900 Amperes, about 1000 Amperes, or any value or range between any two of these values (including endpoints).

It may be understood that the anode and cathode surfaces contacting the first working fluid, the second working fluid, and the third working fluid may be the same set of surfaces or they may differ. If each working fluid contacts an independent pair of anode and cathode surfaces, the respective gap distances may be essentially the same or different, and high voltage electric potentials to which the working fluids are exposed may have essentially the same or different characteristics.

It may be appreciated that each source of the high voltage electric field, such exemplified by plasma torches $102a$, $102b$, and $102c$, may be controlled by one or more control systems. Such control systems may be specific for all the plasma torches $102a$, $102b$, and $102c$ together and may be different from or included with a control system for the entire power generating system. Alternatively, each plasma torch $102a$, $102b$, and $102c$, may have a separate control system. A control system for a plasma torch $102a$, $102b$, and $102c$, may include control functions for torch parameters, such as, but not limited to, the voltage of the high voltage electric field, and a frequency of the high voltage electric field. Control of the torches $102a$, $102b$, and $102c$, may be based on one or more process measurements, including but not limited to, a measurement of a voltage applied to components that may generate the high voltage electric field, a current drain of a voltage supply for the high voltage electric field generators (such as plasma torches $102a$, $102b$, and $102c$), the temperature of the plasma output of the high voltage electric field generators, and the composition of the plasma generated by the high voltage electric field generators. It may further be appreciated that each of the high voltage electric field generators (as exemplified by plasma torches $102a$, $102b$, and $102c$) may be controlled according to one or more process algorithms. The plasma torches $102a$, $102b$, and $102c$ may be controlled according to the same process methods or algorithms (as provided by individual controllers or a single controller). Alternatively, each of the plasma torches $102a$, $102b$, and $102c$ may be controlled according to a different process method or algorithm (as provided by individual controllers or by a single controller).

Each working fluid may be supplied by its own working fluid source. In one non-limiting example, $CO_2$ may be supplied from a $CO_2$ source 104, $O_2$ may be supplied from an $O_2$ source 106, and water vapor ($H_2O$) may be supplied from an $H_2O$ source 108. It may be recognized that control of the fluid plasma from each of the high voltage field sources may also include control the amount of working fluid supplied to each of the high voltage field sources. It is apparent that the working fluid supply sources for the $CO_2$, $O_2$, and $H_2O$ (104, 106, and 108, respectively) may also include control and measurement components. Such components may include, without limitation, components to control the amount of the working fluid supplied by each of the working fluid supply sources (valves) and devices to measure the amount of each of the working fluid supplied (as non-limiting examples, by measuring chemical composition or pressure of the gas delivered). It may be further understood that such measurement and control devices may be controlled by one or more control systems, as disclosed above. Such control systems may be specific to one or more of the working fluid supply sources. Alternatively, all the working fluid supply sources may be controlled by the same control system. In an alternative embodiment, the working fluid supply sources may be controlled by a control system common to the entire fuel generation system. Measurement devices $101a$, $101b$, and $101c$ associated with the first processing chamber 100 may be used by the control systems to control a number of parameters such as amounts of working fluids, voltages associated with the high voltage field generators, and the amount of carbon-based feed-stock admitted into the first processing chamber. Data from such measurement devices may include, without limitation, a temperature $101a$ of the first processing chamber 100, a composition of gases $101b$ within the first processing chamber, and a pressure $101c$ within the first processing chamber.

Although not illustrated in FIG. 1, an alternative embodiment of the system may include three working fluids, such as by $CO_2$, $O_2$, and $H_2O$, that may be combined into one or two combined working fluids before being supplied to one or two high voltage electric field generators. As a non-limiting example, $CO_2$, $O_2$, and $H_2O$ may be combined into a single combined working fluid to be supplied to a single plasma torch. By extension, the controllers associated with each of the supply sources for the $CO_2$, $O_2$, and $H_2O$ (104, 106, and 108, respectively) may cause a specific amount of each gas to be added to the combined working fluid to produce an optimized ratio of gases. Similarly, the controller associated with a single plasma torch may cause the plasma torch to operate under optimum conditions for a specific ratio of gases in the combined working fluid.

The first fluid plasma, the second fluid plasma, and the third fluid plasma together may be directed to contact a carbon-based feed-stock within the first processing chamber, thereby creating a first fluid mixture. The carbon-based feed-stock may be supplied from a carbon-based feed-stock supply 110. The mechanical components used to transport the carbon-based feed-stock into the first processing chamber 100 may be controlled according to some process parameters. The control of the transport of the carbon-based feed-stock may be supplied by a control system. Such a control system may be specific to the mechanical components used to transport the carbon-based feed-stock into the first processing chamber 100. Alternatively, such a control system may be included into a control system to control the entire fuel generation system. Without limitation, examples of the carbon-based feed-stock may include one or more of organic waste (wood chips, sawdust, material made from organic material such as papers, wood furniture), municipal waste, man-made organic material (synthetic carpets, tires, compact discs, plastics, rubbers), coal, carbon, corn, sugar beets, wood, green waste, bagasse, and biomass.

In some non-limiting examples, the first process chamber 100 may also be maintained at a vacuum or near vacuum by a vacuum system 111. The vacuum system 111 may also be controlled by a control system to maintain the pressure within the first process chamber 100. In one non-limiting example, the first process chamber 100 may be maintained at a pressure of about 50 kPa (0.5 atmospheres).

The first fluid mixture, while in the first processing chamber 100, may attain temperatures of about 4000 degrees C. to about 6000 degrees C. Higher or lower temperatures may be attained according to the conditions under which the high voltage field generators operate. The first fluid mixture may be cooled within the first processing chamber 100, at an exit port of the first processing chamber 112, in a transport device (such as a pipe or other duct-work) at an exit of the first processing chamber, or at a combination of these locations through the action of a coolant addition device 114. In one non-limiting example, the coolant may include liquid oxygen (LOX). An amount of coolant introduced into the first fluid mixture by the coolant addition device 114 may be controlled by a control system. In some non-limiting examples, the amount of the coolant added to the first fluid mixture may be controlled according to a temperature of the first fluid mixture, a composition of the first fluid mixture, or other measured parameters of the first fluid mixture. Such a control system may be associated only with the coolant addition device 114. Alternatively, such a control system may be incorporated into a system for controlling the entire fuel generation system. The addition of the coolant to the first fluid mixture may reduce the temperature of the resulting fluid mixture (an admixed first fluid mixture) to about 1450 degrees C. to about 1650 degrees C. It may be further appreciated that the admixed first fluid mixture may have a composition different from that of the first fluid mixture.

The admixed first fluid mixture may be transported to a first heat exchange device 118 where it may exchange at least some of its heat with a heat exchange material, and thus cool to form a second fluid mixture. In some non-limiting examples, the first heat exchange device 118 may be a first heat recovery steam generator (HRSG). The first heat exchange device 118 may allow transfer of at least some heat from the admixed first fluid mixture to a heat exchange material, such as water. Water may enter the first heat exchange device 118 through a first water input port 120 and the amount of water may be controlled by a control system. The heated first heat exchange material, which may include steam as a non-limiting example, may exit the first heat exchange device 118 by means of a first output port 122. In some non-limiting examples, the heated first heat exchange material may be further transported to a first electric turbine to generate a supply of electric power.

In one non-limiting example, the first heat exchange material may be water, which may be converted to a first supply of steam in the first heat exchange device 118. The first supply of steam may activated an electric turbine which may result in the first supply of steam being cooled to liquid water. In some embodiments, the liquid water may be returned to the first heat exchange device 118 to be reheated by more of the admixed first fluid mixture. Alternatively, the first supply of steam, after cooling and condensing, may be returned to a working fluid source 108 to be supplied to a high voltage electric field generator (such as plasma torch 102*c*).

At an output port 126 of the first heat exchange device 118, the second fluid mixture may have a temperature of about 38 degrees C. to about 200 degrees C. The composition of the second fluid mixture may be different from that of the first fluid mixture and that of the admixed first fluid mixture. The components of the second fluid mixture may be separated by a gas separator 128 and the individual components may be directed to individual gas holding containers 129*a*, 129*b*.

The individual components may include one or more of hydrogen gas ($H_2$), and carbon monoxide (CO). The gas separator 128 may comprise, as non-limiting examples, a membrane separation system, a molecular sieve, or a combination thereof. The individual gas holding containers 129*a* and 129*b*, for example an $H_2$ container and a CO container, may each include an outflow metering device 130*a* and 130*b*, respectively. Each outflow metering device 130*a* and 130*b* may be controlled by a controller. Alternatively, the outflow metering devices 130*a* and 130*b* of each of the individual gas holding containers 129*a* and 129*b* may be controlled by the same controller. Each gas holding container 129*a* and 129*b* may also have a gas output port associated with the individual outflow metering devices 130*a* and 130*b*. The gas output port of each of the gas holding containers 129*a* and 129*b* may direct the gas from its gas holding container into a common supply duct 132. Some portion of the second fluid mixture may also be directed into the common supply duct 132.

The outflow metering devices 130*a* and 130*b* of each of the individual gas holding containers 129*a* and 129*b* may be controlled to permit an amount of gas into the common supply duct 132 to create a syngas mixture having a controlled composition. In one non-limiting example, the syngas mixture composition may be controlled based on one or more gas composition sensors 133 associated with the common supply duct 132. In another non-limiting example, the syngas mixture composition may be controlled based on a volume of gas emitted by the outflow metering devices 130*a* and 130*b* of each of the individual gas holding containers 129*a* and 129*b*. In yet another non-limiting example, the syngas mixture composition may be controlled based on the pressure of gas contained in each of the individual gas holding containers 129*a* and 129*b*. In some embodiments, a composition of the syngas may include 1 part CO to 2 parts $H_2$ (1:2). In other embodiments, the ratio of CO to $H_2$ in the syngas may be from about 1:1.2 to about 1:3.

In one non-limiting embodiment, the system may further include a catalyst bed 134 configured to convert the second fluid mixture into a fuel fluid. In a non-limiting example, catalyst bed 134 may include a Fischer-Tropsch type catalyst. In another non-limiting example, the catalyst bed may include one or more of cobalt, iron, ruthenium, nickel, copper, an alkali metal oxide, silica, alumina, and a zeolite. In a system including a catalyst bed 134, the fuel fluid may include one or more of diesel fuel, JP-8 fuel, and aviation fuel. The fuel fluid produced by the system may depend on the material in the catalyst bed 134. Without being bound by theory, non-limiting examples of parameters associated with the catalyst bed 134 that may determine a fuel type production may include catalyst metal composition (such as cobalt, iron, or copper), presence and type of promoter material (such as group 1 alkali metals), available surface area of the catalyst particles, temperature, and pressure. In some non-limiting examples, the catalyst bed 134 may be removable to allow a change in catalyst material to promote one fuel type over another, or to remove exhausted catalyst material.

Fuel from the catalyst bed 134 may be removed and stored in a receptacle 138, and non-reactive gases may be exhausted through an output port 136. The non-reactive gases may be returned to the first processing chamber 100, or separated into components and stored in the individual gas holding containers 129*a* and 129*b*.

A variety of sensors may be associated with the components of the fuel generation system. In some non-limiting embodiments, the sensors may include one or more of a temperature sensor 101*a*, 119*a*, a pressure sensor 101*c*, and a sensor of an amount of a chemical composition 101*b*, 119*b*, 133. In other non-limiting embodiments, the sensors may include one or more of a sensor to measure a temperature of a plasma discharge, a sensor to measure a temperature within the first processing chamber 101*a*, and a sensor to measure a temperature within the first heat exchange device 119*a*. Other non-limiting examples of sensors may include one or more of a sensor to determine an amount of a working fluid delivered to a plasma source, a sensor to determine a composition of a first fluid mixture within the first processing chamber 101*b*, a sensor to determine a composition of a second fluid mixture within the first heat exchange device 119*b*, a sensor to determine a gas pressure within the first processing chamber, and a sensor to determine a gas pressure within the first heat exchange device.

In one non-limiting embodiment, the at least one electronic device of the system may be configured to receive information (data) from the variety of sensors, in which information may include a temperature of a plasma discharge, a temperature within the first processing chamber, a temperature within the first heat exchange device, an amount of a working fluid delivered to a plasma source, a composition of a first fluid mixture within the first processing chamber, a composition of a second fluid mixture within the first heat exchange device, a gas pressure within the first processing chamber, and a gas pressure within the first heat exchange device.

In yet another non-limiting embodiment, the at least one electronic device of the system may be designed to control one or more of a temperature of a plasma discharge, a temperature within the first processing chamber, a temperature within the first heat exchange device, an amount of a working fluid delivered to a plasma source, a gas pressure within the first processing chamber, a gas pressure within the first heat exchange device, and an amount of a carbon-based feedstock delivered into the first processing chamber.

The present disclosure is not to be limited in terms of the particular embodiments described in this application, which are intended as illustrations of various aspects. Many modifications and variations can be made without departing from its spirit and scope, as will be apparent to those skilled in the art. Functionally equivalent methods and apparatuses within the scope of the disclosure, in addition to those enumerated in this disclosure, will be apparent to those skilled in the art from the foregoing descriptions. Such modifications and variations are intended to fall within the scope of the appended claims. The present disclosure is to be limited only by the terms of the appended claims, along with the full scope of equivalents to which such claims are entitled. It is to be understood that this disclosure is not limited to particular methods, reagents, compounds, or compositions, which can, of course, vary. It is also to be understood that the terminology used in this disclosure is for the purpose of describing particular embodiments only, and is not intended to be limiting.

With respect to the use of substantially any plural and/or singular terms in this disclosure, those having skill in the art can translate from the plural to the singular and/or from the singular to the plural as is appropriate to the context and/or application. The various singular/plural permutations may be expressly set forth in this disclosure for sake of clarity. It will be understood by those within the art that, in general, terms used in this disclosure, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). While various compositions, methods, and devices are described in terms of "comprising" various components or steps (interpreted as meaning "including, but not limited to"), the compositions, methods, and devices can also "consist essentially of" or "consist of" the various components and steps, and such terminology should be interpreted as defining essentially closed-member groups.

It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should be interpreted to mean "at least one" or "one or more"); the same holds true for the use of definite articles used to introduce claim recitations. In addition, even if a specific number of an introduced claim recitation is explicitly recited, those skilled in the art will recognize that such recitation should be interpreted to mean at least the recited number (e.g., the bare recitation of "two recitations," without other modifiers, means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

As will be understood by one skilled in the art, for any and all purposes, such as in terms of providing a written description, all ranges disclosed in this disclosure also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed in this disclosure can be readily broken down into a lower third, middle third and upper third, etc. As will also be understood by one skilled in the art all language such as "up to," "at least," and the like include the number recited and refer to ranges which can be subsequently broken down into subranges as discussed above. Finally, as will be understood by one skilled in the art, a range includes each individual member.

From the foregoing, it will be appreciated that various embodiments of the present disclosure have been described for purposes of illustration, and that various modifications may be made without departing from the scope and spirit of the present disclosure. Accordingly, the various embodiments disclosed are not intended to be limiting, with the true scope and spirit being indicated by the following claims.

What is claimed is:

1. A system for synthesizing a fuel fluid, the system comprising: a first processing chamber;
   one or more controllable plasma sources, each of the one or more controllable plasma sources configured to deliver a plasma discharge into the first processing chamber;
   one or more controllable sources of working fluids, each of the one or more controllable sources of working fluids configured to deliver an amount of a working fluid to a corresponding controllable plasma source;
   a vacuum system of the first processing chamber configured to maintain a vacuum pressure within the first processing chamber:
   one or more high voltage electric field generators in the first processing chamber configured to generate one or more high voltage electric fields, wherein each of the one or more high voltage electric fields stabilizes and ionizes the working fluid to generate a fluid plasma;
   a first heat exchange device in fluid communication with the first processing chamber, wherein a first fluid mixture comprising the fluid plasma is directed to the first heat exchange device;
   a coolant addition device in fluid communication with the first processing chamber and the first heat exchange device;
   a gas separator configured to receive a second fluid mixture from an output port of the first heat exchange device and to separate the second fluid mixture into one or more components;
   one or more gas holding containers to store the one or more components of the second fluid mixture, wherein each of the one or more gas holding containers comprises an outflow metering device operably coupled to a common supply duct;
   one or more gas composition sensors operably coupled to the common supply duct and configured to provide information related to a syngas mixture composition to one or more controllers;
   a catalyst bed configured to receive a portion of the one or more components of the second fluid mixture and to convert the portion of the one or more components into a fuel fluid;
   one or more sensors configured to sense at least one process control variable associated with one or more of the first processing chamber, the one or more controllable plasma sources, the one or more of the plurality of controllable sources of working fluids, the coolant addition device, and the first heat exchange device;
   at least one electronic device configured to receive information from the one or more sensors and to control the one or more controllable plasma sources, the one or more of the plurality of controllable sources of working fluids, and the first heat exchange device; and
   at least one receptacle configured to receive the fuel fluid.

2. The system of claim 1, wherein the first processing chamber is maintained at a pressure less than one atmosphere (101 kPa).

3. The system of claim 1, wherein the first processing chamber is maintained at a pressure of about 0.5 atmospheres (51 kPa).

4. The system of claim 1, wherein the plurality of controllable plasma sources comprise a plurality of plasma torches.

5. The system of claim 1, wherein each of the plurality of controllable plasma sources is configured to cause a plasma discharge to contact one or more other plasma discharges, thereby forming the first fluid mixture.

6. The system of claim 1, wherein each of the plurality of controllable plasma sources is configured to maintain a plasma discharge at a temperature of about 7232° F. (4000° C.) to about 36032° F. (20000° C.).

7. The system of claim 1, wherein the plurality of working fluids comprises one or more of: water vapor, carbon dioxide, oxygen, ethanol, methanol, and natural gas.

8. The system of claim 1, further comprising a controllable source of carbon-based feedstock configured to deliver the carbon-based feedstock into the first processing chamber.

9. The system of claim 8, wherein the carbon-based feedstock comprises one or more of the following: carbon, corn, sugar beets wood, green waste, and bagasse.

10. The system of claim 8, wherein each of the plurality of controllable plasma sources is configured to cause a plasma discharge to contact an amount of the carbon-based feedstock, thereby forming the first fluid mixture.

11. The system of claim 10, wherein the first fluid mixture has a temperature of about 7232° F. (4000° C.) to about 36032° F. (20000° C.).

12. The system of claim 10, wherein the first heat exchange device is configured to receive the first fluid mixture.

13. The system of claim 10, wherein the first heat exchange device is configured to cool the first fluid mixture to a temperature of about 100° F. (38° C.) to about 2950° F. (1620° C.), thereby forming the second fluid mixture.

14. The system of claim 13, wherein the components of the second fluid mixture comprise at least carbon monoxide and hydrogen gas.

15. The system of claim 13, wherein the components of the second fluid mixture are combined in the common supply duct, thereby forming a syngas.

16. The system of claim 15, wherein the syngas comprises at least carbon monoxide to hydrogen gas in a ratio of about 1:2.

17. The system of claim 1, wherein the catalyst bed comprises a Fischer-Tropsch catalyst.

18. The system of claim 1, wherein the catalyst bed comprises one or more of the following: cobalt, iron, ruthenium, nickel, copper, an alkali metal oxide, silica, alumina, and a zeolite.

19. The system of claim 1, wherein the fuel fluid comprises one or more of the following: diesel fuel, jet propellant 8 (JP-8) fuel, and jet fuel.

20. The system of claim 1, wherein the plurality of sensors comprise one or more of the following: a temperature sensor, a vacuum sensor, and a sensor of an amount of a chemical composition.

21. The system of claim 1, wherein the plurality of sensors comprise one or more of the following: a sensor to measure a temperature of a plasma discharge, a sensor to measure a temperature within the first processing chamber, and a sensor to measure a temperature within the first heat exchange device.

22. The system of claim 1, wherein the plurality of sensors comprise one or more of the following: a sensor to determine an amount of each of the working fluids delivered to each of the plasma sources, a sensor to determine a composition of the first fluid mixture within the first processing chamber, a sensor to determine a composition of the second fluid mixture within the first heat exchange device, a sensor to determine a gas pressure within the first processing chamber, and a sensor to determine a gas pressure within the first heat exchange device.

23. The system of claim 1, wherein the at least one electronic device is configured to receive information from the plurality of sensors, the information comprising one or more of the following: a temperature of each of the plasma discharges, a temperature within the first processing chamber, a temperature within the first heat exchange device, an amount of each of the working fluids delivered to each of the plasma sources, a composition of the first fluid mixture within the first processing chamber, a composition of the second fluid mixture within the first heat exchange device, a gas pressure within the first processing chamber, and a gas pressure within the first heat exchange device.

24. The system of claim 1, wherein the at least one electronic device is configured to control one or more of the following: a temperature of a plasma discharge, a temperature within the first processing chamber, a temperature within the first heat exchange device, an amount of each of the working fluids delivered to each of the plasma sources, a gas pressure within the first processing chamber, a gas pressure within the first heat exchange device, and an amount of a carbon-based feedstock delivered into the first processing chamber.

* * * * *